United States Patent [19]

Takagishi et al.

[11] Patent Number: 4,621,123

[45] Date of Patent: Nov. 4, 1986

[54] PHOSPHINYLMETHYL POLYPENOLS AND POLYGLYCIDYL ETHERS THEREOF

[75] Inventors: Hisao Takagishi, Kyoto; Kazunori Kawakami, Osaka; Kunimasa Kamio, Suita; Khoichi Okuno, Izumiotsu, all of Japan

[73] Assignee: Sumitomo Chemical Company, Limited, Osaka, Japan

[21] Appl. No.: 809,007

[22] Filed: Dec. 16, 1985

[30] Foreign Application Priority Data

Dec. 20, 1984 [JP] Japan ................................. 59-270086
Dec. 20, 1984 [JP] Japan ................................. 59-270087

[51] Int. Cl.$^4$ ..................... C07D 407/14; C07F 9/53; C08G 61/02
[52] U.S. Cl. ..................... 525/507; 528/99; 528/151; 528/158; 528/167; 528/169; 549/218; 568/15; 568/16
[58] Field of Search ..................... 568/15, 16; 528/99, 528/158, 151, 167, 169; 525/507; 549/218

[56] References Cited

U.S. PATENT DOCUMENTS

| | | | |
|---|---|---|---|
| 3,527,725 | 9/1970 | Strauss et al. | 528/158 |
| 3,745,191 | 7/1973 | Daigle et al. | 528/151 |
| 3,746,758 | 7/1973 | Spivack | 568/15 |
| 4,008,191 | 2/1977 | Jagur-Grodzinski et al. | 528/167 |
| 4,256,844 | 3/1981 | Martin et al. | 528/99 |
| 4,345,059 | 8/1982 | Fretz et al. | 568/15 |

*Primary Examiner*—Veronica P. Hoke
*Attorney, Agent, or Firm*—Stevens, Davis, Miller & Mosher

[57] ABSTRACT

Novel phosphorus-containing polyglycidyl ethers capable of forming a cured epoxy resin having a high flame retardancy and excellent in heat resistance characteristics such as heat deterioration resistance, glass transition temperature, thermal deformation temperature and the like; a process for producing said phosphorus-containing polyglycidyl ethers; phosphorus-containing polyphenol compounds used in production of said phosphorus-containing polyglycidyl ethers; and a process for producing said phosphorus-containing polyphenol compounds.

29 Claims, No Drawings

PHOSPHINYLMETHYL POLYPENOLS AND POLYGLYCIDYL ETHERS THEREOF

BACKGROUND OF THE INVENTION

1. Field of the Invention

The present invention relates to novel phosphorus-containing polyglycidyl ethers as well as a process for producing said compounds. More particularly, the present invention relates to novel phosphorus-containing polyglycidyl ethers capable of forming a cured epoxy resin having a high flame retardancy and excellent in heat resistance characteristics such as heat deterioration resistance, glass transition temperature, thermal deformation temperature and the like, as well as to a process for producing said phosphorus-containing polyglycidyl ethers.

The present invention further relates to phosphorus-containing polyphenol compounds used in production of said phosphorus-containing polyglycidyl ethers, as well as to a process for producing said phosphorus-containing polyphenol compounds.

2. Description of the Prior Art

The recent progress of electric and electronic equipment and apparatuses in integration, performance and reliability is quite remarkable. In response to this movement, insulating materials, parts, etc. used in said equipment and apparatuses are required to have greatly improved properties in heat resistance, moisture resistance, dimensional stability, etc. Moreover, these insulating materials must have flame retardancy as an absolute requirement in view of the safety of electric and electronic equipment and apparatuses.

For allowing the above insulating materials to have flame retardancy, there have conventionally been used so-called brominated epoxy compounds such as diglycidyl ehter of tetrabromobisphenol A, polyglycidyl ether of brominated phenol novolak and the like. These brominated epoxy compounds have a flame-retarding effect but is poor in heat stability and inferior in heat resistance. In addition, these epoxy compounds cause reduction of chemicals resistance, electrical characteristics, etc.

In view of the above situation, the present inventors made an extensive study in order to develop an epoxy compound having flame retardancy and good heat resistance. As a result, the present invention has been completed.

SUMMARY OF THE INVENTION

The present invention provides a phosphorus-containing polyglycidyl ether represented by the following general formula (I)

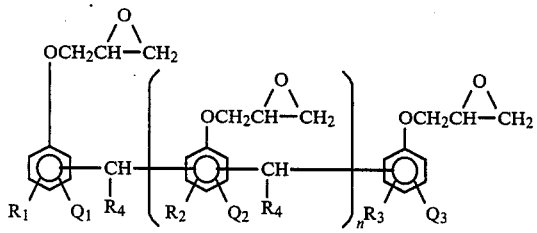

wherein $Q_1$, $Q_2$ and $Q_3$ which may be same or different are a hydrogen atom, an aliphatic group, an aromatic group or a phosphorus-containing group represented by the formula

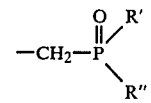

(wherein R' and R'' which may be same or different are an aliphatic group or an aromatic group); at least one of $Q_1$, $Q_2$ and $Q_3$ is said phosphorus-containing group; $R_1$, $R_2$ and $R_3$ which may be same or different are a hydrogen atom, a halogen atom, a glycidyl ether group, an aliphatic group or an aromatic group; $R_4$ is a hydrogen atom or an alkyl group of 1 to 4 carbon atoms; and n is a number of 0 or above, preferably 0 to 18.

The present invention further provides a process for producing a phosphorus-containing polyglycidyl ether represented by the above mentioned general formula (I), which comprises reacting a phosphorus-containing polyphenol compound represented by the following general formula (II)

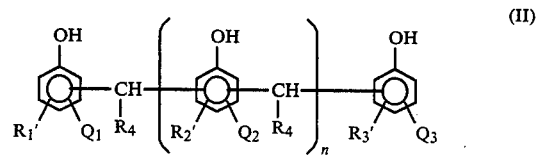

(wherein $Q_1$, $Q_2$, $Q_3$, $R_4$ and n each have the same definition as given above, and $R_1'$, $R_2'$ and $R_3'$ which may be same or different are a hydrogen atom, a halogen atom, a hydroxyl group, an aliphatic group or an aromatic group) with an epihalohydrin.

The present invention furthermore provides a phosphorus-containing polyphenol compound represented by the above mentioned general formula (II).

The present invention furthermore provides a process for producing a phosphorus-containing polyphenol compound represented by the above mentioned general formula (II), which comprises reacting at least one member selected from the phenol compounds represented by the following general formulas (III), (IV) and (V)

-continued

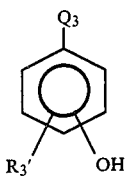
(V)

(wherein $Q_1$, $Q_2$, $Q_3$, $R_1'$, $R_2'$ and $R_3'$ each have the same definition as given above) with an aldehyde represented by the general formula (VI)

$R_4CHO$ (VI)

(wherein $R_4$ has the same definition as given above).

The present invention furthermore provides a process for producing a phosphorus-containing polyphenol compound represented by the above mentioned general formula (II), which comprises reacting a polynuclear phenol represented by the following general formula (VII)

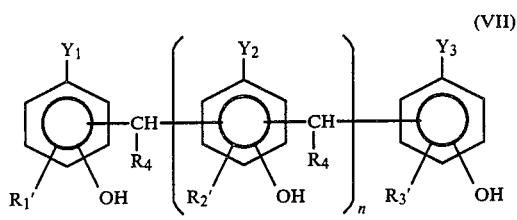
(VII)

[wherein $R_1'$, $R_2'$, $R_3'$, $R_4$ and n each have the same definition as given above: $Y_1$, $Y_2$ and $Y_3$ which may be the same or different are a halogen atom, an aliphatic group, an aromatic group or a substituted methyl group represented by the formula —$CH_2X$ (wherein X is a halogen atom or a hydroxyl group); and at least one of $Y_1$, $Y_2$ and $Y_3$ is said substituted methyl group] with a phosphinite represented by the following general formula (VIII)

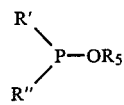
(VIII)

(wherein R' and R" each have the same definition as given above and $R_5$ is an aliphatic group).

DETAILED DESCRIPTION OF THE INVENTION

In the above general formulas, examples of the aliphatic group represented by $Q_1$, $Q_2$ or $Q_3$ include alkyl groups of 1 to 4 carbon atoms such as methyl, ethyl, propyl, butyl and the like; and examples of the aromatic group represented by $Q_1$, $Q_2$ or $Q_3$ include a non-substituted phenyl group and phenyl groups having a lower alkyl substituent such as methyl, ethyl, propyl, butyl or the like.

Examples of the aliphatic group represented by R' or R" include alkyl groups of 1 to 4 carbon atoms such as methyl, ethyl, propyl, butyl and the like. Examples of the aromatic group represented by R' or R" include a non-substituted phenyl group and phenyl groups having a lower alkyl substituent such as methyl, ethyl, propyl, butyl or the like. Preferable as R' or R" are a methyl group, a phenyl group, etc.

The halogen represented by $R_1'$, $R_2'$ or $R_3'$ is chlorine, bromine, etc. As the aliphatic group represented by $R_1'$, $R_2'$ or $R_3'$, there are, for example, alkyl groups of 1 to 10 carbon atoms such as methyl, ethyl, propyl, butyl, octyl, nonyl and the like; lower alkoxy groups such as methoxy, ethoxy and the like; lower alkenyl groups such as allyl, isopropenyl and the like; and aralkyl groups such as benzyl and the like. As the aromatic group represented by $R_1'$, $R_2'$ or $R_3'$, there are, for example, a non-substituted phenyl or phenoxy group and phenyl or phenoxy groups having a lower alkyl substituent such as methyl, ethyl, propyl, butyl or the like.

As the aliphatic group represented by $R_5$, there are mentioned, for example, alkyl groups of 1 to 4 carbon atoms such as methyl, ethyl, propyl, butyl and the like.

Of the phenol compounds represented by the general formula (III), (IV) or (V), a phenol compound containing, as $Q_1$, $Q_2$ or $Q_3$, a phosphorus-containing group represented by the formula

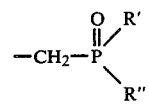

(wherein R' and R" each have the same definition as given above) can be obtained by reacting a compound represented by the general formula (IX)

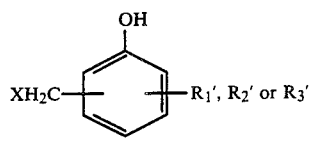
(IX)

(wherein $R_1'$, $R_2'$, $R_3'$ and X each have the same definition as given above) with a phosphinite represented by the general formula (VIII). The amount of phosphinite (VIII) used is 0.5 to 10 moles, preferably 0.8 to 5 moles per 1 mole of the compound of the formula (IX). This reaction can be conducted with heating and stirring, in the absence of any solvent or, if necessary, in the presence of a solvent. The solvent used includes, for example, ethyl ether, tetrahydrofuran, dioxane, benzene, toluene, xylene, acetone, ethyl methyl ketone and methyl isobutyl ketone. The reaction temperature is 20° to 150° C., preferably 30° to 120° C. The reaction time is 1 to 20 hr, preferably 2 to 10 hr.

As the phenol compound having a phosphorus-containing group obtained as above, there can be mentioned (dimethylphosphinylmethyl)phenol, (diethylphosphinylmethyl)phenol, (diphenylphosphinylmethyl)phenol, (methylphenylphosphinylmethyl)phenol, (these compounds have o-, m- and p-isomers), 2-dimethylphosphinylmethyl-5-methoxyphenol, 3-diphenylphosphinylmethyl-6-methoxyphenol, 2-diphenylphosphinylmethyl-5-bromophenol, etc.

As the compound represented by the general formula (III), (IV) or (V) but free from the above mentioned phosphorus-containing group, there can be mentioned phenol, resorcin, hydroquinone, cresol, xylenol, ethylphenol, isopropylphenol, octylphenol, isopropenylphenol, allylphenol, phenylphenol, benzylphenol, chlorophenol, bromophenol, etc. (these compounds have o-, m- and p-isomers).

As specific examples of the aldehyde represented by the general formula (VI), there can be mentioned formaldehyde, acetaldehyde, butyraldehyde, etc.

The reaction between at least one phenol compound represented by the general formula (III), (IV) or (V) and the aldehyde represented by the general formula (VI) can easily be conducted by a polycondensation in the presence of an acid catalyst according to a conventionally known method. As the acid catalyst, there can be used an acid catalyst used in production of an ordinary novolak type phenol resin, and there can specifically be mentioned inorganic acids (e.g. sulfuric acid, hydrochloric acid, phosphoric acid), organic acids (e.g. p-toluenesulfonic acid, oxalic acid) and metal salts (e.g. zinc acetate, zinc chloride, tin tetrachloride). The polycondensation reaction can be conducted in the absence or presence of a solvent. As the solvent, there can be mentioned, for example, toluene, dichlorobenzene, diphenyl ether, butanol, hexanol and cyclohexanol.

The aldehyde represented by the general formula (VI) is used in an amount ordinarily of 0.5 to 1.0 mole, preferably 0.6 to 0.95 mole per 1 mole of total phenols. The acid catalyst is used in an amount ordinarily of 0.001 to 2 moles, preferably 0.01 to 1 mole per 1 mole of total phenols.

The reaction temperature usually is 60° to 200° C., preferably 80° to 150° C. The reaction time differs by factors such as reaction temperature and the like but usually is 1 to 20 hr.

After the reaction, if necessary, neutralization of the catalyst used, etc. are conducted and thereafter the reaction mixture is subjected to distillation with heating to remove water, the solvent used, etc., whereby a phosphorus-containing polyphenol compound (II) is obtained.

The polynuclear phenol represented by the general formula (VII) can be obtained by polycondensing (1) phenol represented by the following general formulas (X), (XI) and (XII)

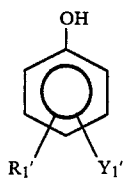   (X)

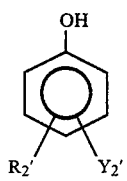   (XI)

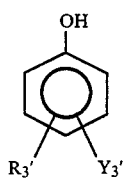   (XII)

(wherein $R_1'$, $R_2'$ and $R_3'$ each have the same definition as given above; $Y_1'$, $Y_2'$ and $Y_3'$ are independently a hydrogen atom, an aliphatic group or an aromatic group; and at least one of $Y_1'$, $Y_2'$ and $Y_3'$ is a hydrogen atom) and (2) an aldehyde represented by the general formula (VI) using an acid catalyst, and then subjecting the resulting polycondensate to methylolation or halomethylation. As specific examples of the polynuclear phenol, there can be mentioned 5,5'-bishydroxymethyl-2,2'-dihydroxy-3,3'-dimethyldiphenylmethane; 3,3'-bishydroxymethyl-2,2'-dihydroxy-5,5'-dimethyldiphenylmethane; 3,3'-bishydroxymethyl-5,5'-dibromo-2,2'-dihydroxydiphenylmethane; and α-hydroxymethyl-ω-hydroxytris[(2-hydroxy-5-methyl-1,3-phenylene)-methylene].

As specific examples of the phosphinite represented by the general formula (VIII), there can be mentioned methyldimethylphosphinite, ethyldimethylphosphinite, methyldiphenylphosphinite and ethyldiphenylphosphinite.

The reaction between the polynuclear phenol (VII) and the phosphinite (VIII) can be conducted with heating and stirring in the absence of any solvent or, if necessary, in the presence of a solvent. As the solvent used, there can be mentioned, for example, ethyl ether, tetrahydrofuran, dioxane, benzene, toluene, xylene, acetone, ethyl methyl ketone and methyl isobutyl ketone. The reaction temperature is 20° to 150° C., preferably 30° to 120° C. The phosphinite (VIII) is used in an amount of 0.5 to 10 moles, preferably 0.8 to 5 moles per 1 equivalent of the substituted methyl group of the polynuclear phenol (VII).

The phosphorus-containing polyglycidyl ether represented by the general formula (I) can be produced by reacting the phosphorus-containing polyphenol compound (II) obtained as above with an epihalohydrin.

As the epihalohydrin used, there can be mentioned, for example, epichlorohydrin, epibromohydrin and epiiodohydrin. Epichlorohydrin is preferable for industrial use. The epihalohydrin is used in an amount usually of 2 to 50 moles, preferably 3 to 25 moles per 1 equivalent of the phenolic hydroxyl group of the phosphorus-containing polyphenol compound (II).

As the method for reacting a polynuclear phenol (VII) and a phosphinite (VIII), there are (1) one step method wherein an addition reaction and a dehydrohalogenation reaction are conducted simultaneously using an alkali and (2) two step method wherein an addition reaction is conducted firstly using a catalyst such as a quaternary ammonium salt, a tertiary amine or the like and then a dehydrohalogenation reaction is conducted using an alkali. Either method can be used. As the alkali used, there can be mentioned, for example, sodium hydroxide, potassium hydroxide, calcium hydroxide and potassium carbonate. Preferable of these are sodium hydroxide and potassium hydroxide. Specific examples of the catalyst include quaternary ammonium salts such as tetramethylammonium chloride, tetraethylammonium bromide, trimethylbenzylammonium chloride and the like as well as tertiary amines such as benzyldimethylamine, triethylamine, N,N,N',N'-tetramethylethylenediamine and the like. The alkali is used in an amount usually of 0.8 to 1.4 moles, preferably 0.9 to 1.3 moles per 1 equivalent of the phenolic hydroxyl group of the phosphorus-containing polyphenol compound (II). The catalyst is used in an amount usually of 0.001 to 1 mole, preferably 0.005 to 0.5 mole per 1 equivalent of said phenolic hydroxyl group.

The reaction temperature is 30° to 130° C., preferably 40° to 120° C. It is preferable that the reaction be allowed to proceed with removing the water formed in the reaction out of the reaction system.

After the reaction, salts formed as by-product are removed by filtration or the like and excessive epihalohydrin is removed by distillation, whereby an intended product is obtained.

Like ordinary epoxy compounds, the polyglycidyl ether (I) of the present invention can be cured, alone or in combination with other epoxy compound, by a curing agent such as a polyamine type curing agent (e.g. an aliphatic polyamine, an aromatic polyamine, a polyamide polyamine), an acid anhydride type curing agent (e.g. hexahydrophthalic anhydride, methyltetrahydrophthalic anhydride, a phenol type curing agent (e.g. phenol novolak, cresol novolak), a Lewis acid (e.g. boron trifluoride) or its salt, a dicyandiamide, a polymercaptan or the like. In curing, in addition to the curing agent, there can be incorporated into the polyglycidyl ether, as necessary, various other additives such as a curing accelerator, an inorganic or organic filler, a lubricant and the like. The cured epoxy resin obtained by using the polyglycidyl ether (I) of the present invention can be used in wide application fields requiring flame retardancy. Specific examples of these application fields include insulating materials, laminated sheets, sealing materials, molding materials and composite materials.

The phosphorus-containing polyglycidyl ether (I) of the present invention can further be efficiently used, alone or in combination with other substance, as a characteristic improver (e.g. a flame retardant, an antioxidant, an ultraviolet deterioration inhibitor, a coloring inhibitor) for a variety of synthetic resins such as polyolefins, polystyrenes, polyvinyl chlorides, ABS resins, polysulfones, polyesters, phenol resins and the like. The polyglycidyl ether of the present invention can furthermore be effectively used as a thermal stability improver, a flame retardant or the like for synthetic fibers mainly composed of a polyacrylonitrile, a polyester, a polyamide, etc.

The phosphorus-containing polyphenol compound (II) of the present invention can be incorporated into curable resins such as epoxy resins, urethane resins, urea resins, melamine resins, polybismaleimide resins, alkyd resins, ordinary phenol resins and the like, to obtain a curable resin composition with excellent flame retardancy. The phosphorus-containing polyphenol compound (II) can also be used as a flame retardant of additive type for synthetic fibers such as polyesters, polyamides, polyacrylonitriles and the like as well as for synthetic resins such as polyolefins, polystyrenes, ABS resins and the like.

Further there can be provided a novel thermosetting resin of flame-retarding type, by subjecting the compound (II) to modification such as glycidyl etherification (which is one of the subject matters of the present invention), allyl etherification or the like.

Hereunder the present invention will be described in more detail by way of Examples. However, the present invention is in no way restricted to these Examples.

REFERENCE EXAMPLE 1

Synthesis of o-(diphenylphosphinylmethyl)phenol

In a reactor equipped with a thermometer, a stirrer and a condenser were placed 99.2 g of o-(hydroxymethyl)phenol and 400 ml of tetrahydrofuran. They were made into a uniform solution. Thereto was added 184 g of ethyldiphenylphosphinite. The resulting mixture was subjected to reaction for 3 hr with heating and stirring. The reaction mixture was cooled and the resulting white crystal precipitate was separated by filtration and then dried to obtain 180 g of o-(diphenylphosphinylmethyl)phenol. Yield: 73% Melting point: 179° C.

REFERENCE EXAMPLE 2

Synthesis of p-(diphenylphosphinylmethyl)phenol

Reaction was conducted in the same manner as in Reference Example 1 except that 99.2 g of p-(hydroxymethyl)phenol was used in place of 99.2 g of o-(hydroxymethyl)phenol to obtain 160 g of a white crystal of p-(diphenylphosphinylmethyl)phenol. Yield: 65% Melting point: 125° C.

REFERENCE EXAMPLE 3

Synthesis of o-(diethylphosphinylmethyl)phenol

Reaction was conducted in the same manner as in Reference Example 1 except that 107.2 g of ethyldiethylphosphinite was used in place of 184 g of ethyldiphenylphosphinite to obtain 144 g of a white crystal of o-(diethylphosphinylmethyl)phenol. Yield: 85% Melting point: 127° C.

REFERENCE EXAMPLE 4

Synthesis of 3,3'-bishydroxymethyl-2,2'-dihydroxy-5,5'-dimethyldiphenylmethane

In a reactor equipped with a thermometer, a stirrer and a condenser were placed 540 g of p-cresol, 80 g of 37.7% formalin and 20 g of 36% hydrochloric acid. The resulting mixture was subjected to reaction for 4 hr at 60° to 65° C. The system was heated under a vacuum to distill off the water and the unreacted p-cresol both present in the system, after which there was obtained under a vacuum of 3 mmHg, as a fraction having a boiling point of 200° to 205° C., 142 g of 2,2'-dihydroxy-5,5'-dimethyldiphenylmethane. Upon cooling, the compound solidified. Melting point: 124° C.

Next, in a reactor of the same type were placed 1,350 g of water and 40 g of 20% aqueous sodium hydroxide solution. Nitrogen was blown thereinto. Thereto was added 114 g of 2,2'-dihydroxy-5,5'-dimethyldiphenylmethane and the mixture was made into a uniform solution. Then, 119 g of 37.7% formalin was added. The whole mixture was subjected to reaction for 2 hr at 72° to 75° C. The reaction mixture was cooled to 30° C. and carbon dioxide gas was blown thereinto. Blowing of carbon dioxide gas was stopped when the pH of the system became 7.1. The resulting white precipitate was obtained by filtration, washed with water thoroughly, vacuum-dried at room temperature and recrystallized from 1,2-dichloroethane to obtain 118 g of 3,3'-bishydroxymethyl-2,2'-dihydroxy-5,5'-dimethyldiphenyl methane. Melting point: 147° C.

SYNTHESIS OF PHOSPHORUS-CONTAINING POLYPHENOL COMPOUNDS

Example 1

In a reactor equipped with a thermometer, a stirrer and a condenser were placed 92.4 g of o-(diphenylphosphinylmethyl)phenol obtained in Reference Example 1, 19 g of p-toluenesulfonic acid monohydrate and 60 ml of n-butanol. This mixture was stirred at 105° C. to make it into a uniform solution. Thereto was added 19.5 g of 37% formalin. The resulting mixture was subjected to reaction for 7 hr at 100° to 110° C. Then, 20 g of 20% aqueous sodium hydroxide solution was added to neutralize the catalyst. The water layer was separated and removed. The remaining layer was concentrated under a vacuum to remove water, n-butanol, etc., whereby 93.4 g of a resin was obtained. This resin had a softening point of 162° C.

According to gel permeation chromatography, the resin had a number average molecular weight $\overline{Mn}$ of 1,340 in terms of polystyrene and a molecular weight distribution ($\overline{Mw}/\overline{Mn}$) of 1.4.

The resin was dissolved in dimethylsulfoxide-$d_6$ and measured for $^1H$ NMR spectrum. The result is shown in Table 1.

From the results the resin was ascertained to be a novolak of o-(diphenylphosphinylmethyl)phenol. The resin had the following recurring unit structure.

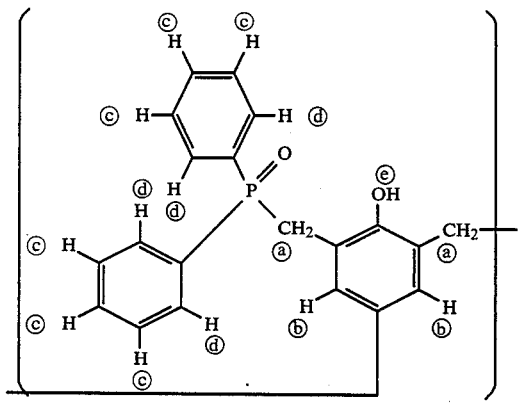

TABLE 1

| δ value (ppm, TMS standard) | Peak assignment |
|---|---|
| 3.5–4.0 | a |
| 6.3–7.9 | b |
| 7.3–7.6 | c |
| 7.7–7.9 | d |
| 9.5–9.7 | e |

Example 2

Reaction was conducted in the same manner as in Example 1 except that 92.4 g of p-(diphenylphosphinylmethyl)phenol obtained in Reference Example 2 was used in place of o-(diphenylphosphinylmethyl)phenol, whereby 94.1 g of a resin was obtained. This resin was a novolak of p-(diphenylphosphinylmethyl)phenol.

Example 3

In a reactor of the same type as used in Example 1 were placed 106 g of o-(diethylphosphinylmethyl)phenol obtained in Reference Example 3, 5 ml of 35% hydrochloric acid and 100 ml of n-butanol. This mixture was heated to 100° C. to make it a uniform solution. Thereto was added 32.4 g of 37% formalin, and reaction was conducted for 6 hr at 100° to 110° C. The water layer was separated and removed. The remaining layer was concentrated under a vacuum to obtain 108.6 g of a resin. The resin was a novolak of o-(diethylphosphinyl-methyl)phenol.

Example 4

In a reactor of the same type as used in Example 1 were placed 61.6 g of o-(diphenylphosphinylmethyl)phenol obtained in Reference Example 1, 21.6 g of o-cresol, 8 ml of conc. hydrochloric acid and 100 ml of toluene. This mixture was stirred with heating to make it a uniform solution.

Thereto was added 26 g of 37% formalin, and the resulting mixture was subjected to reaction for 10 hr at 100° to 105° C. Then, the water layer was separated and removed. The remaining layer was concentrated under a vacuum to obtain 86 g of a resin. The resin was an o-(diphenylphosphinylmethyl)phenol/o-cresol copolymer novolak.

Example 5

In a reactor of the same type as used in Example 1 were placed 115.2 g of 3,3'-bishydroxymethyl-2,2'-dihydroxy-5,5'-dimethyldiphenylmethane obtained in Reference Example 4 and 500 ml of tetrahydrofuran. They were made into a uniform solution. Thereto was added 184 g of ethyldiphenylphosphinite. The resulting mixture was subjected to reaction for 4 hr at 67° to 70° C. After completion of the reaction, the reaction mixture was cooled, and the resulting white crystal precipitate was obtained by filtration and dried. There was obtained 233 g of a white crystal. Yield: 88.8% Melting point: 221° C.

The results of the elementary analysis for the white crystal are shown in Table 2.

TABLE 2

| | Elementary analysis | |
|---|---|---|
| | Measured | Calculated |
| Carbon | 74.8% | 75.0% |
| Hydrogen | 5.8% | 5.8% |
| Phosphorus | 9.6% | 9.5% |

Mass spectrometry revealed that the white crystal has a molecular weight of 656. The crystal was dissolved in $CDCl_3$ and measured for $^1H$ NMR spectrum, which results are shown in Table 3. From these results, the crystal was ascertained to have the following molecular structure.

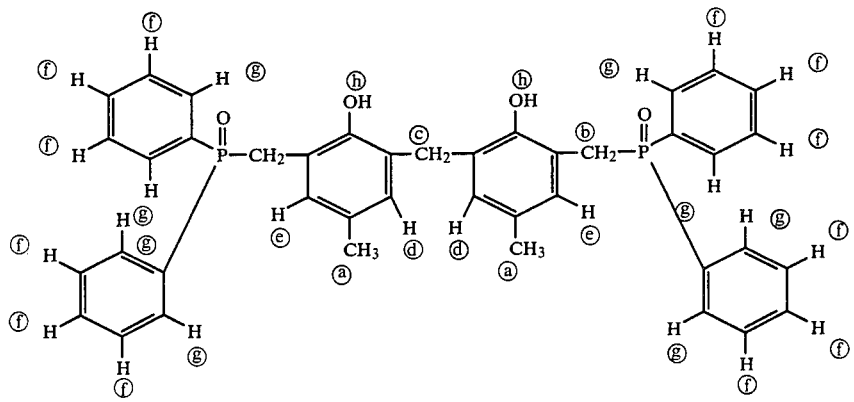

| δ value<br>(ppm, TMS standard) | Peak<br>assignment | Intensity<br>ratio |
| --- | --- | --- |
| 2.1 | a | 3 |
| 3.65–3.7 | b | 2 |
| 3.9 | c | 1 |
| 6.65 | d | 1 |
| 6.85 | e | 1 |
| 7.4–7.5 | f | 6 |
| 7.7–7.8 | g | 4 |
| 9.5 | h | 1 |

SYNTHESIS OF PHOSPHORUS-CONTAINING POLYGLYCIDYL ETHERS

Example 6

In a reactor equipped with a thermometer, a stirrer, a dropping funnel and a device for separation of formed water were placed 80 g of a novolak of o-(diphenylphosphinylmethyl)phenol obtained in Example 1 and 350 g of epichlorohydrin. The reactor inside was then purged with nitrogen. The reaction system was adjusted to a pressure of 150 mmHg and gradually heated to a boiling point. In this condition, 21 g of 48% aqueous sodium hydroxide solution was dropped over a period of 4 hr. During this time, the reaction temperature was kept at 62° to 64° C. and water was removed from the reaction system in the form of an azeotropic mixture with epichlorohydrin. The distilled and recovered epichlorohydrin was recirculated. After completion of the reaction, by-produced salts were removed by filtration and the filtrate was concentrated to obtain 89.5 g of a light yellow resin having an epoxy equivalent of 421 g/eq and a softening point of 132° C. The resin had a phosphorus content of 8.0%.

Gel permeation chromatography revealed that the resin had a number average molecular weight $\overline{Mn}$ of 1,420 and a molecular weight distribution ($\overline{Mw}/\overline{Mn}$) of 1.6.

The resin was dissolved in a dimethylsulfoxide-$d_6$ and measured for $^1H$ NMR spectrum. The results are shown in Table 4.

From these results, the above resin was ascertained to be a polyglycidyl ether of o-(diphenylphosphinylmethyl)phenol novolak and have the following recurring unit structure.

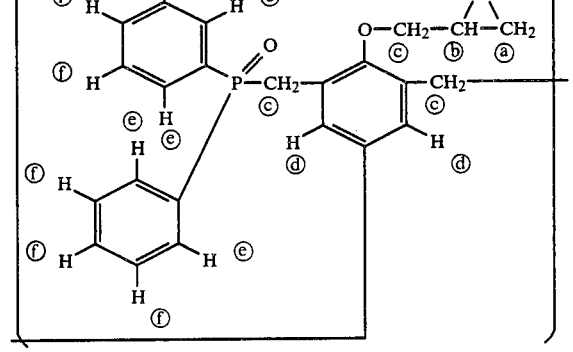

| δ value<br>(ppm, TMS standard) | Peak<br>assignment |
| --- | --- |
| 2.65–2.85 | a |
| 3.2 | b |
| 3.5–4.1 | c |
| 6.5–6.95 | d |
| 7.4–7.5 | e |
| 7.7–7.8 | f |

Example 7

In a reactor of the same type as used in Example 1 were placed 131.2 g of the phosphorus-containing polyphenol obtained in Example 5 and 740 g of epichlorohydrin. The reactor inside was then purged with nitrogen. The reaction system was adjusted to a pressure of 250 mmHg and gradually heated to a boiling point. In this condition, 34 g of 48% aqueous sodium hydroxide solution was dropped over a period of 3 hr. During this time, the reaction temperature was kept at 75° to 78° C. and water was removed from the reaction system in the form of an azeotropic mixture with epichlorohydrin. After completion of the reaction, by-produced salts were removed by filtration and the filtrate was concentrated. The concentrate was recrystallized from acetone to obtain 109 g of a white crystal having an epoxy equivalent of 386 g/eq and a melting point of 182° C.

The white crystal had the elementary analysis values as shown in Table 5.

TABLE 5

| | Elementary analysis | |
|---|---|---|
| | Measured | Calculated |
| Carbon | 73.2% | 73.4% |
| Hydrogen | 6.1% | 6.0% |
| Phosphorus | 8.1% | 8.1% |

Mass spectrometry revealed that the white crystal has a molecular weight of 768. The crystal was dissolved in chloroform-d and measured for $^1H$ NMR spectrum. The results are shown in Table 6. From these results, the white crystal was ascertained to be a diglycidyl ether having the following molecular structure.

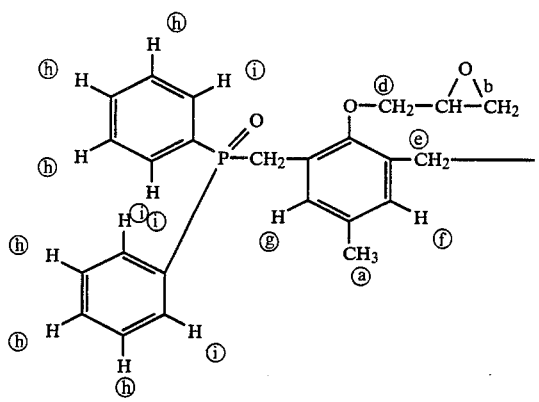
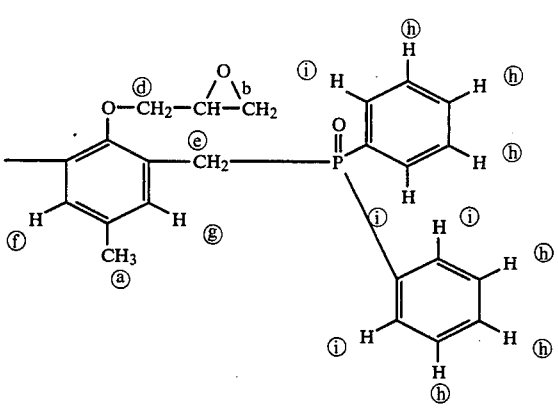

TABLE 6

| δ value (ppm, TMS standard) | Peak assignment | Intensity ratio |
|---|---|---|
| 2.1 | a | 3 |
| 2.65–2.85 | b | 2 |
| 3.25 | c | 1 |
| 3.5–3.6, 4.0–4.05 | d | 2 |
| 3.7–3.8 | e | 3 |
| 6.5 | f | 1 |
| 7.0 | g | 1 |
| 7.4–7.5 | h | 6 |
| 7.75–7.85 | i | 4 |

REFERENCE EXAMPLE 5

Into an epoxy resin of bisphenol A type (Sumiepoxy ELA-128 manufactured by SUMITOMO CHEMICAL CO., LTD.) was incorporated a phosphorus-containing polyglycidyl ether obtained in Example 6 or Example 7. Thereto was added $BF_3 \cdot MEA$ (boron trifluoride-monoethylamine complex) as a curing agent and the resulting composition was cured with heating. The cured composition was measured for flame retardancy and glass transition temperature.

A composition using, as a flame retardant, an epoxy resin of tetrabromobisphenol A type (Sumiepoxy ESB-400 manufactured by SUMITOMO CHEMICAL CO., LTD.), a composition using, as a flame retardant, triphenylphosphine oxide of non-reactive nature, and a composition using no flame retardant were cured and measured for the same test items.

The compounding ratios of these compositions and the measurement results are shown in Table 7.

As is obvious from Table 7, the cured compositions using the compounds of the present invention are excellent in flame resistance and heat resistance.

TABLE 7

| | Run No. in Reference Example 5 | | | | | | |
|---|---|---|---|---|---|---|---|
| | Present Invention | | | | Comparative Examples | | |
| | 1 | 2 | 3 | 4 | 5 | 6 | 7 |
| Compounding ratio, weight ratio | | | | | | | |
| Sumiepoxy ELA-128 | 60 | 50 | 60 | 50 | 50 | 60 | 100 |
| Polyglycidyl ether of Example 6 | 40 | 50 | — | — | — | — | — |
| Polyglycidyl ether of Example 7 | — | — | 40 | 50 | — | — | — |
| Sumiepoxy ESB-400*[1] | — | — | — | — | 50 | — | — |
| Triphenylphosphine oxide | — | — | — | — | — | 40 | — |
| $BF_3 \cdot MEA$ | 3 | 3 | 3 | 3 | 3 | 3 | 3 |
| Phosphorus/bromine contents, % | 3.1/0 | 3.9/0 | 3.1/0 | 3.9/0 | 0/23.5 | 4.3/0 | 0/0 |
| Curing condition | 130° C. × 2 hr + 170° C. × 2 hr | | | | | | |
| Flame resistance*[2] | | | | | | | |
| Burning time, sec | 3 | 1 | 2 | 1 | 2 | 1 | >180 |
| Burning distance, mm | 7 | 6 | 6 | 5 | 9 | 6 | >75 |
| Glass transition temperature, °C. | 152 | 150 | 148 | 148 | 130 | 67 | 133 |

*[1]Epoxy equivalent: 398 g/eq, Bromine content: 48.2%
*[2]According to JIS K-6911

What is claimed is:

1. A phosphorus-containing polyglycidyl ether represented by the following general formula (I)

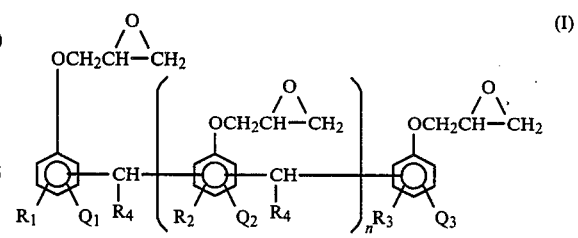

wherein $Q_1$, $Q_2$ and $Q_3$ which may be same or different are a hydrogen atom, an aliphatic group, an aromatic group or a phosphorus-containing group represented by the formula

wherein R' and R" which may be same or different are an aliphatic group or an aromatic group; at least one of $Q_1$, $Q_2$ and $Q_3$ is said phosphorus-containing group; $R_1$, $R_2$ and $R_3$ which may be same or different are a hydrogen atom, a halogen atom, a glycidyl ether group, an aliphatic group or an aromatic group; $R_4$ is a hydrogen atom or an alkyl group of 1 to 4 carbon atoms; and n is a number of 0 or above.

2. A phosphorus-containing polyglycidyl ether according to claim 1, wherein the aliphatic group represented by $Q_1$, $Q_2$, $Q_3$, R', R", $R_1$, $R_2$ or $R_3$ is an alkyl group of 1 to 4 carbon atoms, the aromatic group represented by $Q_1$, $Q_2$, $Q_3$, R', R", $R_1$, $R_2$ or $R_3$ is a non-substituted or lower alkyl-substituted phenyl group and n is 0 to 18.

3. A process for producing a phosphorus-containing polyglycidyl ether represented by the following general formula (I)

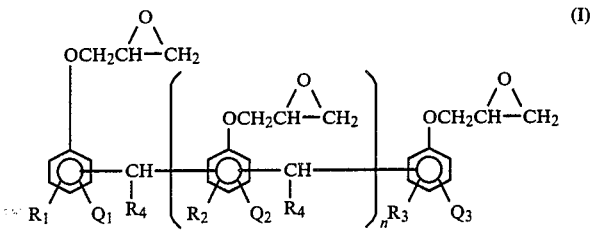

wherein $Q_1$, $Q_2$ and $Q_3$ which may be same or different are a hydrogen atom, an aliphatic group, an aromatic group or a phosphorus-containing group represented by the formula

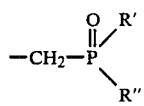

wherein R' and R" which may be same or different are an aliphatic group or an aromatic group; at least one of $Q_1$, $Q_2$ and $Q_3$ is said phosphorus-containing group; $R_1$, $R_2$ and $R_3$ which may be same or different are a hydrogen atom, a halogen atom, a glycidyl ether group, an aliphatic group or an aromatic group; $R_4$ is a hydrogen atom or an alkyl group of 1 to 4 carbon atoms; and n is a number of 0 or above, the process comprising reacting a phosphorus-containing polyphenol compound represented by the following general formula (II)

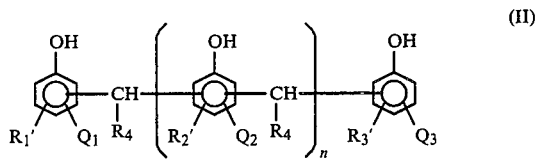

wherein $Q_1$, $Q_2$, $Q_3$, $R_4$ and n each have the same definition as given above, and $R_1'$, $R_2'$ and $R_3'$ which may be same or different are a hydrogen atom, a halogen atom, a hydroxyl group, an aliphatic group or an aromatic group with an epihalohydrin.

4. A process according to claim 3, wherein the aliphatic group represented by $Q_1$, $Q_2$, $Q_3$, R', R", $R_1$, $R_2$ or $R_3$ is an alkyl group of 1 to 4 carbon atoms, the aromatic group represented by $Q_1$, $Q_2$, $Q_3$, R', R", $R_1$, $R_2$ or $R_3$ is a non-substituted or lower alkyl-substituted phenyl group and n is 0 to 18.

5. A process according to claim 3, wherein the epihalohydrin is epichlorohydrin, epibromohydrin or epiiodohydrin.

6. A process according to claim 3, wherein the epihalohydrin is used in an amount of 2 to 50 moles per 1 equivalent of the phenolic hydroxyl group of the phosphorus-containing polyphenol compound.

7. A process according to claim 3, wherein the reaction of the phosphorus-containing polyphenol compound and the epihalohydrin is conducted by (1) one step method wherein an addition reaction and a dehydrohalogenation reaction are conducted simultaneously using an alkali or (2) two step method wherein an addition reaction is firstly conducted using a quaternary ammoniumm salt or a tertiary amine as a catalyst and then a dehydrohalogenation is conducted using an alkali.

8. A process according to claim 7, wherein the alkali is sodium hydroxide, potassim hydroxide, calcium hydroxide or potassium carbonate.

9. A process according to claim 7, wherein the quaternary ammonium salt is tetramethylammonium chloride, tetraethylammonium bromide, tetraethylammonium bromide or trimethylbenzylammonium chloride.

10. A process according to claim 7, wherein the alkali is used in an amount of 0.8 to 1.4 moles per 1 equivalent of the phenolic hydroxyl group of the phosphorus-containing polyphenol compound.

11. A process according to claim 7, wherein the catalyst is used in an amount of 0.001 to 1 mole per 1 equivalent of the phenolic hydroxyl group of the phosphorus-containing polyphenol compound.

12. A process according to claim 7, wherein the reaction is conducted at 30° to 130° C.

13. A phosphorus-containing polyphenol compound represented by the following general formula (II)

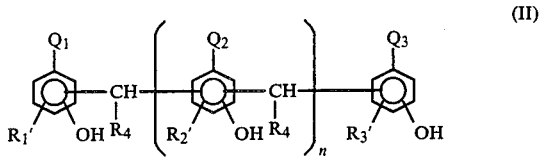

wherein $Q_1$, $Q_2$ and $Q_3$ which may be same or different are a hydrogen atom, an aliphatic group, an aromatic group or a phosphorus-containing group represented by the formula

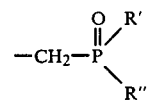

wherein R' and R" which may be same or different are an aliphatic group or an aromatic group; at least one of $Q_1$, $Q_2$ and $Q_3$ is said phosphorus-containing group; $R_1'$, $R_2'$ and $R_3'$ which may be same or different are a hydrogen atom, a halogen atom, a hydroxyl group, an aliphatic group or an aromatic group; $R_4$ is a hydrogen atom or an alkyl group of 1 to 4 carbon atoms; and n is a number of 0 or above.

14. A phosphorus-containing polyphenol compound according to claim 13, wherein the aliphatic group represented by $Q_1$, $Q_2$, $Q_3$, R', R", $R_1'$, $R_2'$ or $R_3'$ is an alkyl group of 1 to 4 carbon atoms, the aromatic group represented by $Q_1$, $Q_2$, $Q_3$, $R'$, $R''$, $R_1'$, $R_2'$ or $R_3'$ is a non-substituted or lower alkyl-substituted phenol group, and n is 0 to 18.

15. A process for producing a phosphorus-containing phenol compound represented by the following general formula (II)

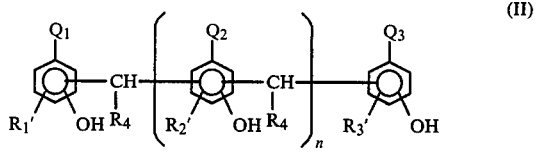

(II)

wherein $Q_1$, $Q_2$ and $Q_3$ which may be same or different are a hydrogen atom, an aliphatic group, an aromatic group or a phosphorus-containing group represented by the formula

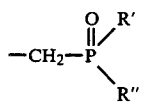

wherein $R'$ and $R''$ which may be same or different are an aliphatic group or an aromatic group; at least one of $Q_1$, $Q_2$ and $Q_3$ is said phosphorus-containing group; $R_1'$, $R_2'$ and $R_3'$ which may be same or different are a hydrogen atom, a halogen atom, a hydroxyl group, an aliphatic group or an aromatic group; $R_4$ is a hydrogen atom or an alkyl group of 1 to 4 carbon atoms; and n is a number of 0 or above, the process comprising reacting at least one member selected from the phenol compounds represented by the general formulas (III), (IV) and (V)

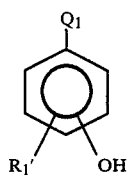

(III)

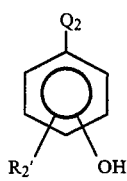

(IV)

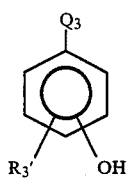

(V)

wherein $Q_1$, $Q_2$, $Q_3$, $R_1'$, $R_2'$ and $R_3'$ each have the same definition as given above with an aldehyde represented by the general formula (VI)

 R$_4$CHO (VI)

wherein $R_4$ has the same definition as given above.

16. A process according to claim 15, wherein the aliphatic group represented by $Q_1$, $Q_2$, $Q_3$, $R'$, $R''$, $R_1'$,
$R_2'$ or $R_3'$ is an alkyl group of 1 to 4 carbon atoms, the aromatic group represented by $Q_1$, $Q_2$, $Q_3$, $R'$, $R''$, $R_1'$, $R_2'$ or $R_3'$ is a non-substituted or lower alkyl-substituted phenyl group, and n is 0 to 18.

17. A process according to claim 15, wherein the phenol compound represented by the general formula (III), (IV) or (V) is phenol, resorcin, hydroquinone, cresol, xylenol, ethylphenol, isopropylphenol, octylphenol, isopropenylphenol, allylphenol, phenylphenol, benzylphenol, chlorophenol or bromophenol.

18. A process according to claim 15, wherein the aldehyde represented by the general formula (VI) is formaldehyde, acetaldehyde or butyraldehyde.

19. A process according to claim 15, wherein the reaction between the phenol compound and the aldehyde is conducted in the presence of an acid catalyst.

20. A process according to claim 19, wherein the acid catalyst is sulfuric acid, hydrochloric acid, phosphoric acid, p-toluenesulfonic acid, oxalic acid, zinc acetate, zinc chloride or tin tetrachloride.

21. A process according to claim 15, wherein the aldehyde represented by the general formula (VI) is used in an amount of 0.5 to 1.0 mole per 1 mole of total phenol components.

22. A process according to claim 19, wherein the acid catalyst is used in an amount of 0.001 to 2 moles per 1 mole of total phenol components.

23. A process according to claim 15, wherein the reaction is conducted at 60° to 200° C. for 1 to 20 hr.

24. A process for producing a phosphorus-containing polyphenol compound represented by the following general formula (II)

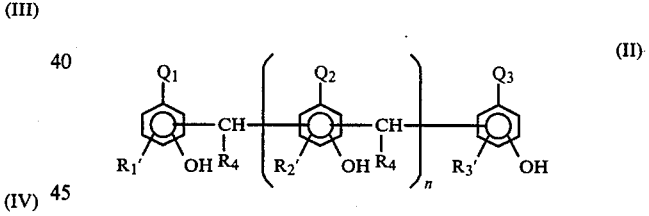

(II)

wherein $Q_1$, $Q_2$ and $Q_3$ which may be same or different are a hydrogen atom, an aliphatic group, an aromatic group or a phosphorus-containing group represented by the formula

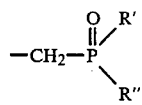

wherein $R'$ and $R''$ which may be same or different are an aliphatic group or an aromatic group; at least one of $Q_1$, $Q_2$ and $Q_3$ is said phosphorus-containing group; $R_1'$, $R_2'$ and $R_3'$ which may be same or different are a hydrogen atom, a halogen atom, a hydroxyl group, an aliphatic group or an aromatic group; $R_4$ is a hydrogen atom or an alkyl group of 1 to 4 carbon atoms; and n is a number of 0 or above, the process comprising reacting a polynuclear phenol represented by the general formula (VII)

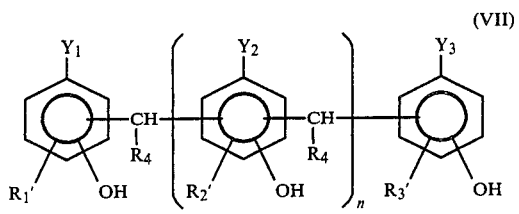

wherein $R_1'$, $R_2'$, $R_3'$, $R_4$ and n each have the same definition as given above; $Y_1$, $Y_2$ and $Y_3$ which may be same or different are a hydrogen atom, an aliphatic group, an aromatic group or a substituted methyl group represented by —CH$_2$X wherein X is a halogen atom or a hydroxyl group; and at least one of $Y_1$, $Y_2$ and $Y_3$ is said substituted methyl group, with a phosphinite represented by the following general formula (VIII)

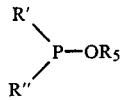

wherein R' and R" which may be same or different are an aliphatic group or an aromatic group and $R_5$ is an aliphatic group.

25. A process according to claim 24, wherein the aliphatic group represented by $Q_1$, $Q_2$, $Q_3$, R', R", $R_1'$, $R_2'$ or $R_3'$ is an alkyl group of 1 to 4 carbon atoms, the aromatic group represented by $Q_1$, $Q_2$, $Q_3$, R', R", $R_1'$, $R_2'$ or $R_3'$ is a non-substituted or lower alkyl-substituted phenyl group, and n is 0 to 18.

26. A process according to claim 24, wherein the polynuclear phenol represented by the general formula (VII) is 5,5'-bishydroxymethyl-2,2'-dihydroxy-3,3'-dimethyldiphenylmethane, 3,3'-bishydroxymethyl-2,2'-dihydroxy-5,5'-dimethyldiphenylmethane, 3,3'-bishydroxymethyl-5,5'-dibromo-2,2'-dihydroxydiphenylmethane or α-hydroxymethyl-ω-hydroxy-tris[(2-hydroxy-5-methyl-1,3-phenylene)methylene].

27. A process according to claim 24, wherein the phosphinite represented by the general formula (VIII) is methyldimethylphosphinite, ethyldimethylphosphinite, methyldiphenylphosphinite or ethyldiphenylphosphinite.

28. A process according to claim 24, wherein the phosphinite (VIII) is used in an amount of 0.5 to 10 moles per 1 equivalent of the substituted methyl group of the polynuclear phenol (VII).

29. A process according to claim 24, wherein the reaction is conducted at 20° to 150° C.

* * * * *